United States Patent
Ooto (10) Patent No.: US 9,612,000 B2
(45) Date of Patent: Apr. 4, 2017

(54) LIGHT SOURCE DEVICE INCLUDING PHASE MATCHING ELEMENT FOR MEASURING THE DEGREE OF OXYGEN SATURATION IN BLOOD

(75) Inventor: Masanori Ooto, Yokohama (JP)

(73) Assignee: FUJI ELECTRIC CO., LTD., Kawasaki-Shi (JP)

(*) Notice: Subject to any disclaimer, the term of this patent is extended or adjusted under 35 U.S.C. 154(b) by 323 days.

(21) Appl. No.: 13/634,823

(22) PCT Filed: Jun. 24, 2011

(86) PCT No.: PCT/JP2011/003616
§ 371 (c)(1),
(2), (4) Date: Dec. 10, 2012

(87) PCT Pub. No.: WO2012/029225
PCT Pub. Date: Mar. 8, 2012

(65) Prior Publication Data
US 2013/0083325 A1    Apr. 4, 2013

(30) Foreign Application Priority Data
Sep. 3, 2010   (JP) ................................ 2010-198044

(51) Int. Cl.
*F21V 9/00*     (2015.01)
*G01N 21/55*    (2014.01)
(Continued)

(52) U.S. Cl.
CPC ............ *F21V 9/00* (2013.01); *A61B 5/14552* (2013.01); *G01N 21/55* (2013.01); *A61B 3/12* (2013.01);
(Continued)

(58) Field of Classification Search
CPC ......... A61B 3/12; A61B 5/14552; F21V 9/00; G01N 21/55; G02F 1/3558;
(Continued)

(56) References Cited

U.S. PATENT DOCUMENTS 5,082,363 A * 1/1992 Nakanishi et al. .......... 356/3.04
7,065,035 B1   6/2006 Mizuuchi et al.
(Continued)

FOREIGN PATENT DOCUMENTS

JP    2001-194695 A    7/2001
JP    2001-290182 A    10/2001
(Continued)

OTHER PUBLICATIONS

Japanese Patent Office Action issued Jan. 29, 2013 and the English Translation thereof.

*Primary Examiner* — Kara E Geisel
*Assistant Examiner* — Violeta A Prieto
(74) *Attorney, Agent, or Firm* — Rabin & Berdo, P.C.

(57) ABSTRACT

This light source device includes one light emission unit from which light is emitted, plural light source units, a photo coupler, and a control unit. The plural light source units output outgoing lights with mutually differing wavelengths. The photo coupler connects the light emission unit and plural light source units. The control unit controls the plural light source units via a driver. Each of the plural light source units includes a light emitting element and a wavelength conversion unit. The wavelength conversion unit converts the wavelength of light output from the light emitting element, thus generating the outgoing light.

7 Claims, 7 Drawing Sheets

(51) Int. Cl.
  *A61B 5/1455*   (2006.01)
  *A61B 3/12*     (2006.01)
  *G02F 1/355*    (2006.01)
  *G02F 1/35*     (2006.01)

(52) U.S. Cl.
  CPC .... *G02F 1/3558* (2013.01); *G02F 2001/3507* (2013.01)

(58) Field of Classification Search
  CPC .......... G02F 2001/3507; G02F 1/3544; G02F 2001/3546; G02F 2001/3548; G02F 1/3532; G02F 1/37
  USPC .................. 356/300–334, 402–425
  See application file for complete search history.

(56) References Cited

U.S. PATENT DOCUMENTS

| | | |
|---|---|---|
| 2004/0095982 A1 | 5/2004 | Momiuchi et al. |
| 2006/0161140 A1 | 7/2006 | Hayashi et al. |
| 2006/0193231 A1* | 8/2006 | Mizuuchi et al. ............. 369/94 |
| 2007/0078449 A1 | 4/2007 | Hayashi et al. |
| 2007/0219439 A1 | 9/2007 | Vilser et al. |
| 2010/0157311 A1 | 6/2010 | Hayashi et al. |

FOREIGN PATENT DOCUMENTS

| | | |
|---|---|---|
| JP | 2002-323628 A | 11/2002 |
| JP | 2004-172314 A | 6/2004 |
| JP | 2006-189587 A | 7/2006 |
| JP | 2007-097629 A | 4/2007 |
| JP | 2007-147688 A | 6/2007 |
| JP | 2007-530186 A | 11/2007 |
| JP | 2009-042197 A | 2/2009 |
| WO | WO-2005/094671 A1 | 10/2005 |

* cited by examiner

LIGHT SOURCE DEVICE INCLUDING PHASE MATCHING ELEMENT FOR MEASURING THE DEGREE OF OXYGEN SATURATION IN BLOOD

CROSS-REFERENCE TO RELATED APPLICATIONS

This application is the national phase of international application number PCT/JP2011/003616, filed Jun. 24, 2011, and claims the benefit of priority of Japanese patent application JP PA 2010-198044, filed Sep. 3, 2010. The disclosures of the international application and the Japanese priority application are incorporated herein by reference.

BACKGROUND

Technical Field

The present invention relates to a light source device that can change the wavelength of outgoing light, and can emit outgoing lights of various wavelengths from the same optical axis.

Background Art

In recent years, spectroscopic analysis using a laser light of two wavelengths or more has started to be put to practical use. For example, there is a method whereby, when detecting the concentration of a certain component, the difference in intensity between a wavelength absorbed by the component and transmitted light of a wavelength that is not absorbed is detected. This kind of two wavelength or more laser spectrometry is implemented utilizing not only absorption by a detected component, but also optical characteristics such as scattering and reflection.

With the heretofore described spectroscopic analysis using laser light, it is often the case that a laser diode is commonly used in measuring in an infrared region. In an infrared region, it is comparatively easy to fabricate a laser diode of any wavelength using a DFB structure, or the like.

Meanwhile, with, for example, spectroscopic analysis of a component inside a human body, or the like, there is a desire to carry out spectroscopic analysis using the wavelength of visible light. However, as no appropriate light source exists for visible light, it is difficult to implement the heretofore described spectroscopic analysis in these regions (in particular, 490 nm to 630 nm).

A method of obtaining a light source of visible light of 490 nm to 630 nm is commonly implemented using wavelength conversion. For example, in JP-A-2004-172314, there is described a method whereby visible light of two wavelengths is obtained by exciting a solid laser medium using a laser diode, generating two different kinds of fundamental wave, and subsequently converting the wavelengths with a non-linear crystal. As described in this document, in order that the optical axis is the same, spatial light coupling with a half mirror is used.

Also, as described in JP-A-2007-97629, plural visible lights having mutually differing wavelengths are obtained by generating plural fundamental waves using plural fiber amplifiers as laser media, and converting the wavelengths of the fundamental waves with a non-linear crystal. As described in this document, in order that the optical axis is the same, a light switch configured of fiber is used.

With the technologies described in JP-A-2004-172314 and JP-A-2007-97629, plural fundamental waves are generated by exciting a laser medium, and the wavelengths of the fundamental waves are converted. When using a laser medium in this way, time is needed for a stimulated emission from the laser medium, meaning that modulation speed decreases.

SUMMARY

The invention, having been contrived bearing in mind the heretofore described circumstances, has an object of providing a light source device with which it is possible to emit outgoing lights with plural wavelengths from the same optical axis, and possible to modulate the outgoing lights at high speed.

Alight source device according to the invention includes a light emission unit, plural light source units, a photo coupler, and a control unit. Light is emitted from the light emission unit. The plural light source units output outgoing lights with mutually differing wavelengths. The coupler connects the light emission unit and plural light source units. The control unit controls the plural light source units. Each of the plural light source units includes a light emitting element, and a wavelength conversion unit that converts the wavelength of light output from the light emitting element, thus generating the outgoing light.

In the light source device, the wavelengths of the outgoing lights output by the plural light source units are, for example, 490 nm or more, 630 nm or less. Also, the control unit may cause at least two of the light source units to operate simultaneously, thus causing at least two kinds of the outgoing light to be emitted simultaneously from the light emission unit.

Light emitted from the light emission unit is used as, for example, a light source for measuring the saturated oxygen concentration of blood. In this case, the light source device may further include a detection unit. The detection unit detects the intensity of reflected light generated by light emitted from the light emission unit being reflected by a measurement target. Then, the control unit gradually increases the output of the light emitting element, and stops the increase of the output of the light emitting element when the intensity of the reflected light detected by the detection unit reaches a threshold value or above.

Also, the wavelength conversion unit has, for example, a quasi phase matching element.

According to the invention, it is possible to provide alight source device with which it is possible to emit outgoing lights with plural wavelengths from the same optical axis, and possible to modulate the outgoing lights at high speed.

BRIEF DESCRIPTION OF THE DRAWINGS

The heretofore described object, other objects, characteristics, and advantages will be further clarified by preferred embodiments described hereafter, and by the following drawings pertaining to the embodiments.

DETAILED DESCRIPTION

Hereafter, a description will be given, using the drawings, of embodiments of the invention. The same reference numerals and signs are given to identical components in all the drawings, and a description is omitted as appropriate.

(First Embodiment)

Figure 1:
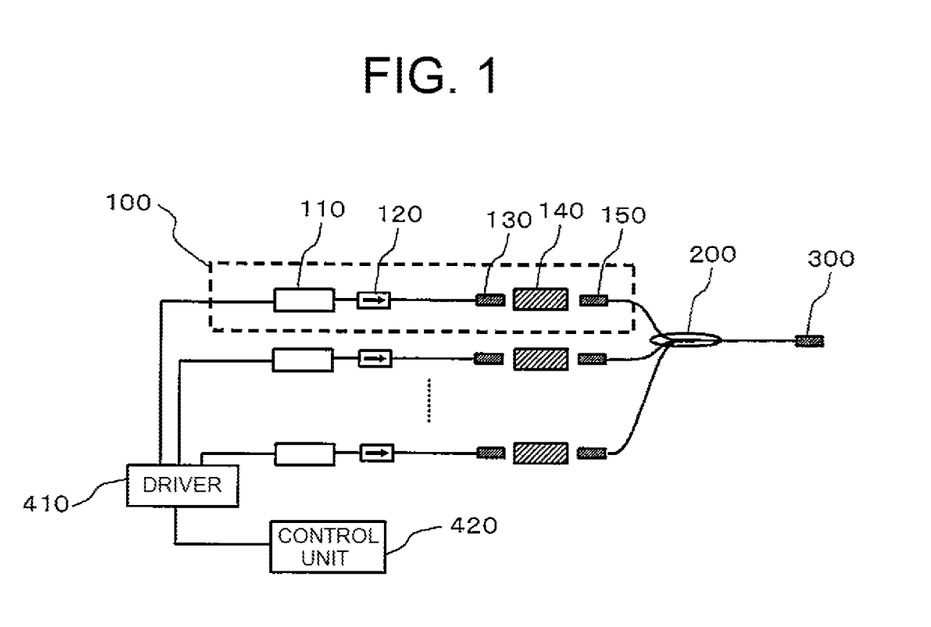
FIG. 1 is a diagram showing a configuration of a light source device according to a first embodiment.

FIG. 1 is a diagram showing a configuration of a light source device according to a first embodiment. The light source device includes one light emission unit 300 from which light is emitted, plural light source units 100, a photo coupler 200, and a control unit 420. The plural light source units 100 output outgoing lights of mutually differing wavelengths. The photo coupler 200 connects the light emission unit 300 and the plural light source units 100. The control unit 420 controls the plural light source units 100 via a driver 410. The plural light source units 100 each includes a light emitting element 110 and a wavelength conversion unit 140. The wavelength conversion unit 140 converts the wavelength of light output from the light emitting element, thus generating outgoing light. Hereafter, a detailed description will be given.

In the embodiment, the light emitting element 110 of the light source unit 100 is a semiconductor laser such as, for example, a pump laser diode. The wavelength of light output by the light emitting element 110 is, for example, 980 nm or more, 1,260 nm or less. The light output from the light emitting element 110 is conducted to an optical system 130 using an optical fiber. An isolator 120 is provided partway along the optical fiber. The isolator 120 prevents light reflected by the optical system 130 or an end portion of the optical fiber from returning to the light emitting element 110. Because of this, the operation of the light emitting element 110 is stable. Light output from the optical system 130 falls incident on the wavelength conversion unit 140.

The wavelength conversion unit 140 has a wavelength conversion element such as, for example, a quasi phase matching element, a birefringent phase phasic matching element, a non-linear crystal, a photonic crystal, a non-linear optical fiber, or a photonic crystal optical fiber, and generates outgoing light of the light source unit 100 by converting light output by the light emitting element 110 in such a way as to shorten the wavelength thereof. The wavelength of the outgoing light differs for each light source unit 100. In the embodiment, the wavelength of the outgoing light of each light source unit 100 is 490 nm or more, 630 nm or less in every case. Light output from the wavelength conversion unit 140 is introduced into an optical fiber via an optical system 150. The light introduced into the optical fiber is conducted to the photo coupler 200.

The photo coupler 200 gathers outgoing light from each light source unit 100 into one optical axis, and introduces it into one optical fiber. The light introduced into the optical fiber is emitted to the exterior from the light emission unit 300. The photo coupler 200 may be configured of a multi-mode optical fiber, or may be configured of a single-mode optical fiber. In the latter case, it is possible to cut a high-order mode of short wavelength light.

The light emitting element 110 of each light source unit 100 emits light as a result of power being input from the driver 410. At what timing the driver 410 causes which light emitting element 110 to emit light is controlled by the control unit 420. The driver 410 controls an output (including a turning on and off) of a fundamental wave of the light emitting element 110 by controlling, for example, current input into the light emitting element 110. Also, by modulating the current input into the light emitting element 110, it is possible to modulate the intensity of light output from the light emitting element 110. Because of this, it is possible to add an intensity modulation to light emitted from the light emission unit 300.

Next, a description will be given of an operation of the light emitting element according to the embodiment. When wishing to cause a single light to be emitted from the light emission unit 300, the control unit 420 causes the driver 410 to select the light source unit 100 that outputs a desired wavelength, and causes power to be supplied to the light emitting element 110 of the selected light source unit 100. Because of this, the light emitting element 110 to which power is supplied emits light. Then, the wavelength of the light emitted by the light emitting element 110 is converted by the wavelength conversion unit 140, and the light is emitted from the light emission unit 300 via the photo coupler 200.

Then, when wishing to change the wavelength of the light emitted from the light emission unit 300, the control unit 420 causes the driver 410 to change the selected light source unit 100, and causes power to be supplied to the light emitting element 110 of the light source unit 100 after the change. Because of this, the wavelength of the light emitted from the light emission unit 300 is changed at high speed.

Also, when wishing to cause plural outgoing lights to be emitted simultaneously from the light emission unit 300, the control unit 420 causes the driver 410 to select the plural light source units 100, and causes power to be supplied to the light emitting element 110 of each of the selected light source units 100.

Figure 2:
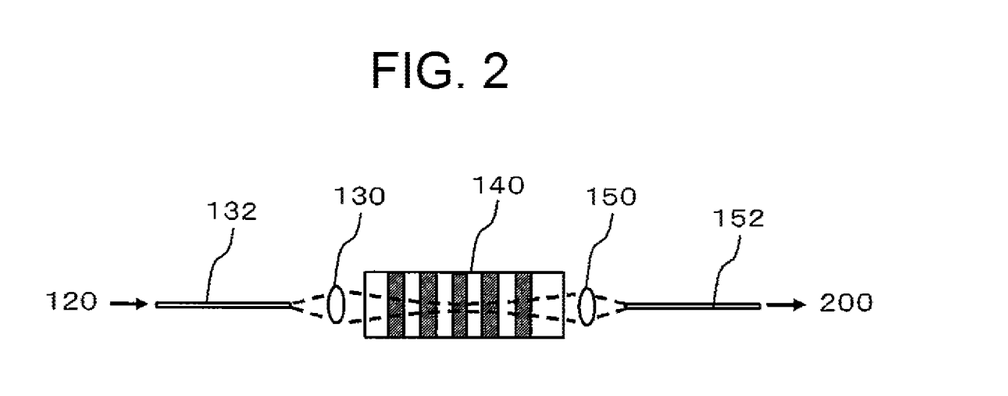
FIG. 2 is a diagram showing a configuration of the periphery of a wavelength conversion unit when using a bulk-type quasi phase matching element as the wavelength conversion unit.

FIG. 2 is a diagram showing a configuration of the periphery of the wavelength conversion unit 140 when using a bulk-type quasi phase matching element as the wavelength conversion unit 140. Light coming via the isolator 120 is radiated from an end portion of an optical fiber 132. The radiated light is focused by the optical system 130, and falls incident on the quasi phase matching element acting as the wavelength conversion unit 140. Then, light radiated from the quasi phase matching element is focused by the optical system 150, and falls incident on an optical fiber 152.

Figure 3:
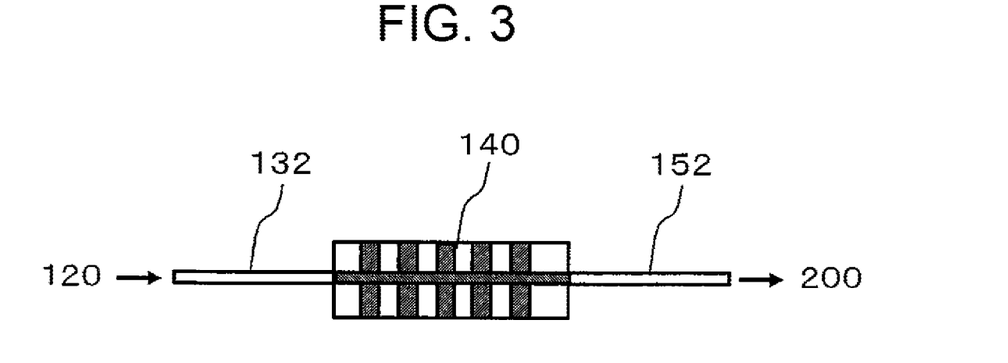
FIG. 3 is a diagram showing a configuration of the periphery of the wavelength conversion unit when using a waveguide-type quasi phase matching element as the wavelength conversion unit.

As shown in FIG. 3, when using a waveguide-type quasi phase matching element as the wavelength conversion unit 140, the optical fibers 132 and 152 may be connected directly to the waveguide of the quasi phase matching element, without passing through optical systems.

Next, a description will be given of actions and advantages of the embodiment.

For example, laser beams of mutually differing wavelengths being emitted from the same optical axis, modulation being of a high speed, wavelength switching speed being high, and the like, are included as being important as light source characteristics in spectroscopic analysis. Also, the configuration being simple, small, and low-cost are also important from an industrial aspect.

The reason that emission from the same optical axis is advantageous is that it is advantageous to increase measurement position accuracy. When there is unevenness in detected components due to the measurement position, it is not possible to carry out accurate measurement when there is misalignment of the beam path.

The reason that high-speed modulation is advantageous is that, as the laser spectroscopic measurements are high-sensitivity measurements of a weak light, it is advantageous to use a high-sensitivity detection method utilizing high-speed light source modulation.

The reason that high-speed wavelength switching is advantageous is that it is advantageous to implement measurement at plural wavelengths at intervals short enough not to impair the temporal stability of measured components.

In response to these demands, it is possible, according to the embodiment, to emit outgoing lights of plural wavelengths from the same optical axis. Also, as the light emitting element 110 is used as a light emission source, it is possible to carry out modulation of the outgoing lights at high speed. Furthermore, as it is possible to change the wavelength of the outgoing light emitted from the light emission unit 300 by changing the light emitting element 110 to which the driver 410 supplies power, wavelength switching speed is high. Also, as the light emitting element 110 and wavelength conversion unit 140 occupy the major portion of the optical system, it is possible for the configuration of the light source device to be simple, small, and low-cost.

(Second Embodiment)

Figure 4:
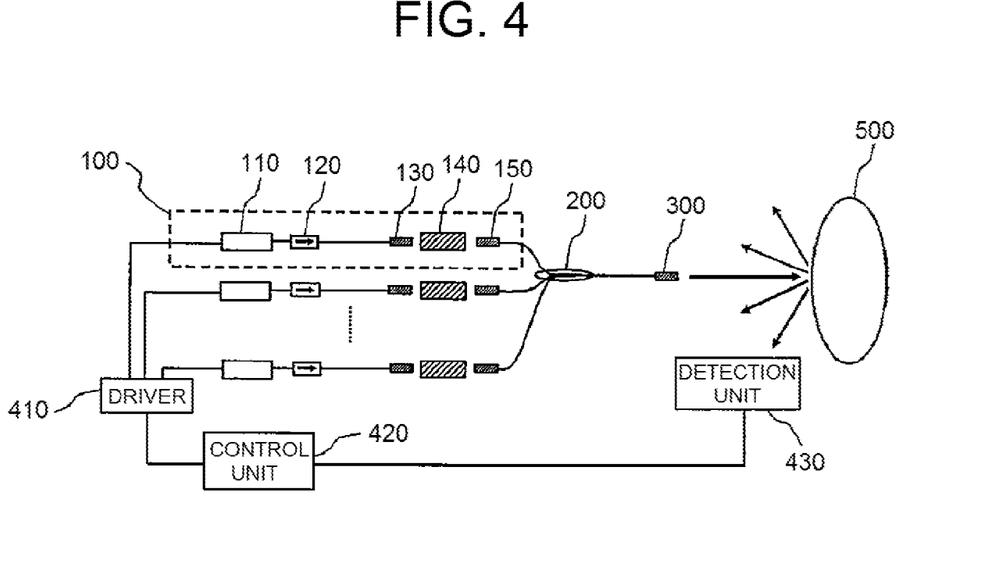
FIG. 4 is a diagram showing a configuration of a light source device according to a second embodiment.

FIG. 4 is a diagram showing a configuration of a light source device according to a second embodiment. The light source device is used as a device that non-invasively measures the saturated oxygen concentration of blood, and has the same configuration as the optical device according to the first embodiment, except for including a detection unit 430. Outgoing light emitted from the light emission unit 300 of the light source device is caused to irradiate a measurement target 500 (for example, a human eye fundus, or the like). The outgoing light used in the irradiation is diffused and reflected in the measurement target 500, after which it is emitted from the measurement target 500. At this time, as the outgoing light proceeds a certain distance inside the measurement target 500, one portion of the light is absorbed by the blood inside the measurement target 500. Then, the detection unit 430 measures the intensity of the diffused and reflected light emitted from the measurement target 500, and outputs the intensity to the control unit 420.

Figure 5:
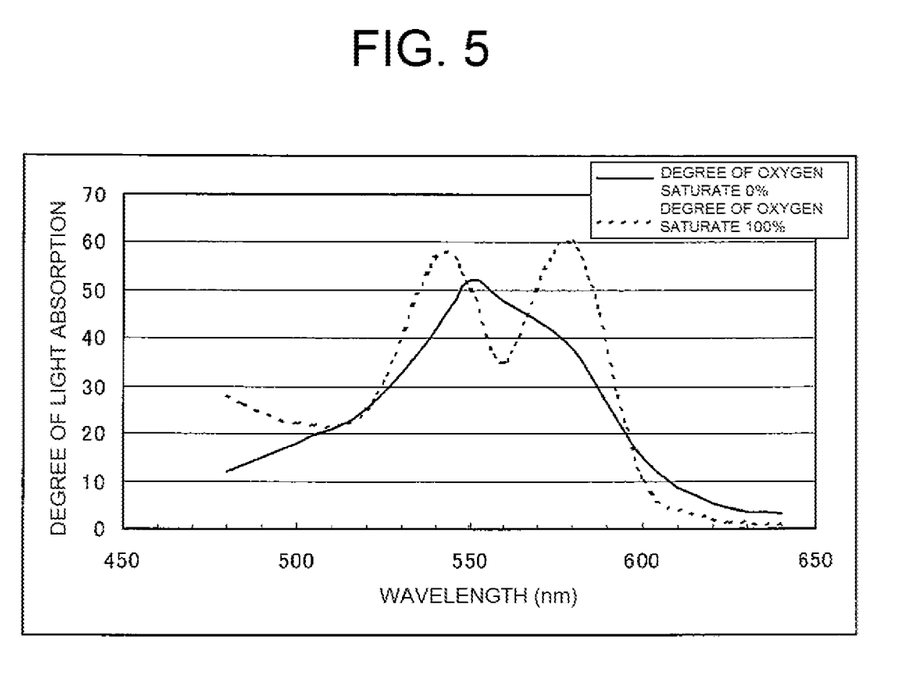
FIG. 5 is a diagram showing an example of absorption spectra in a visible region of blood.

It is known that absorption spectra in a visible region of blood differ depending on the degree of oxygen saturation. For example, in a wavelength range of 500 nm to 600 nm, there is one absorption peak when the degree of oxygen saturation is 0%, while there are two absorption peaks when the degree of oxygen saturation is 100%, as shown in FIG. 5. Because of this, by investigating in advance the degree of absorption at a certain specific wavelength by degree of oxygen saturation, and investigating the degree of absorption by the blood of an inspection target at that specific wavelength, it is possible to measure the degree of oxygen saturation of the blood of the inspection target. The computing process is carried out by the control unit 420.

Herein, it is often the case that plural specific wavelengths are used, with the object of increasing detection accuracy. For example, there are cases in which two wavelengths of 540 nm and 560 nm are used as specific wavelengths, and there are also cases in which two wavelengths of 560 nm and 580 nm are used. Also, three wavelengths of 540 nm, 560 nm, and 580 nm may be used as specific wavelengths. The wavelengths selected as specific wavelengths are not limited to the examples above.

Also, when carrying out a detection of the degree of oxygen saturation, it is important to carry out the measurement in a site in which there are a large number of capillary vessels. The reasons for this are that a large amount of blood vessel rupture that causes severe damage to the human body occurs in sites in which there are a large number of capillary vessels, and that a connection between blood vessel rupture and the degree of oxygen saturation in the blood has been pointed out in recent years. Meanwhile, it is also necessary to increase both spatial resolution and temporal resolution in portions in which there are a large number of capillary vessels. When carrying out measurements in mutually differing sites, the accuracy of the measurement results decreases. Also, as an organism is constantly moving slightly, and the flow of blood does not stop, it is necessary when using plural specific wavelengths to carry out a measurement using each specific wavelength at the same timing.

In response to this, in the light source device according to the embodiment, plural specific wavelengths are emitted on the same optical axis from one light emission unit 300 by the plural light source units 100 being driven simultaneously. Also, the detection unit 430 can measure the light intensity of the plural wavelengths simultaneously. Because of this, it is possible to measure the absorption spectra of plural specific wavelengths at the same timing, and for the same measurement target 500.

As the degree of light absorption changes considerably depending on the degree of oxygen saturation, it is preferable to adjust the intensity of outgoing light appropriate for the measurement in accordance with the degree of oxygen saturation. This is because although, in general, measurement accuracy is improved by increasing the amount of light falling incident on measured components, in the case of a living organism measurement, it is desirable in terms of non-invasiveness that the amount of measurement light falling incident is lower.

Figure 6:
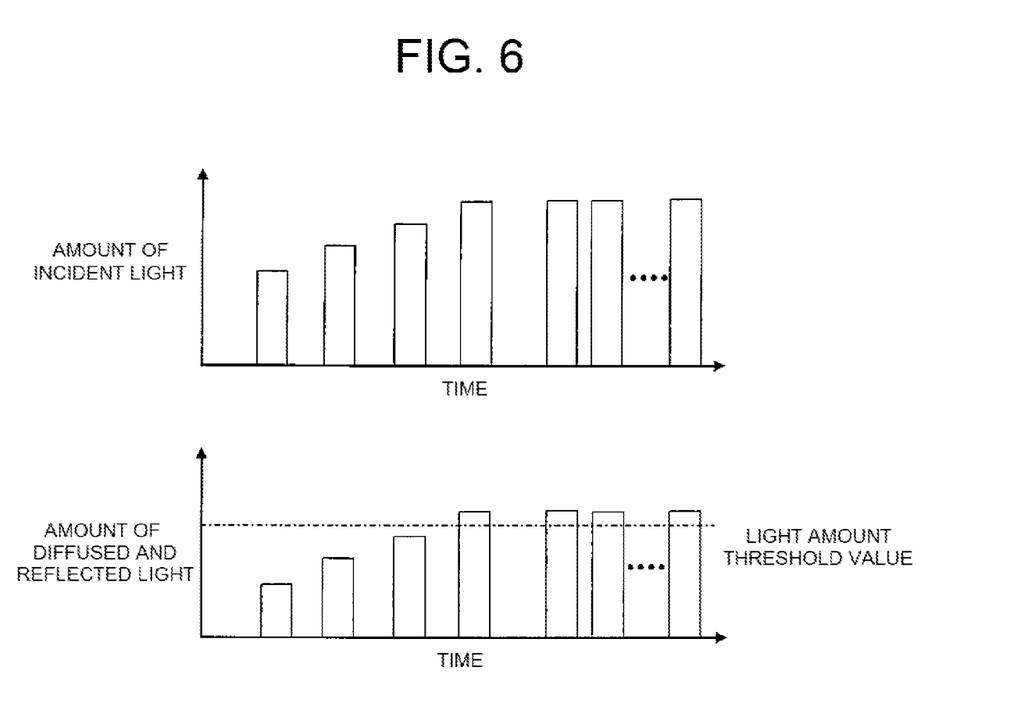
FIG. 6 is a diagram illustrating an example of control by a control unit.

In response to this, in the embodiment, the control unit 420 controls the light emitting element 110 of the light source unit, via the driver 410, in the following way, as shown in FIG. 6. An intensity of diffused and reflected light at which it is possible to ensure measurement accuracy is input in advance into the control unit 420 as a threshold value. Then, the control unit 420 monitors the intensity of the diffused and reflected light detected by the detection unit 430 while gradually increasing the output of the light emitting element 110 from a somewhat low value. Then, the control unit 420 stops increasing the output of the light emitting element 110 at a point at which the intensity of the diffused and reflected light exceeds the threshold value, and implements a measurement in that state for a certain time, at a predetermined frequency. By carrying out this kind of control, it is possible to detect the concentration of saturated oxygen in the blood with higher sensitivity. Herein, when carrying out a lock-in detection, or the like, that has a modulation frequency as a reference in the detection unit 430, it is possible to carry out a more highly sensitive measurement.

The heretofore described method can also be applied when simultaneously driving the plural light source units 100, thus causing lights with plural specific wavelengths to be emitted on the same optical axis from the light emission unit 300. Also, although the modulated waveform of the modulated light is rectangular, it may also be a sinusoidal wave, a triangular waveform, a sawtooth waveform, or the like.

WORKING EXAMPLE 1

In the light source device according to the first embodiment, two light source units 100 are driven simultaneously. A wavelength λ1 of light output by the light emitting element 110 included in a first light source unit 100 is 1,240 nm, while a wavelength λ2 of light output by the light emitting element 110 included in a second light source unit 100 is 1,064 nm. A quasi phase matching element of lithium niobate, cyclically subjected to a polarization inversion, is used as the wavelength conversion unit 140, and the outgoing light of each light source unit 100 is a second harmonic wave. An end surface of the quasi phase matching element is coated with an antireflection film effective against a fundamental wave and a harmonic wave of a third order or higher. Also, a single mode fiber is used as fiber forming the light emission unit 300.

Figure 7:
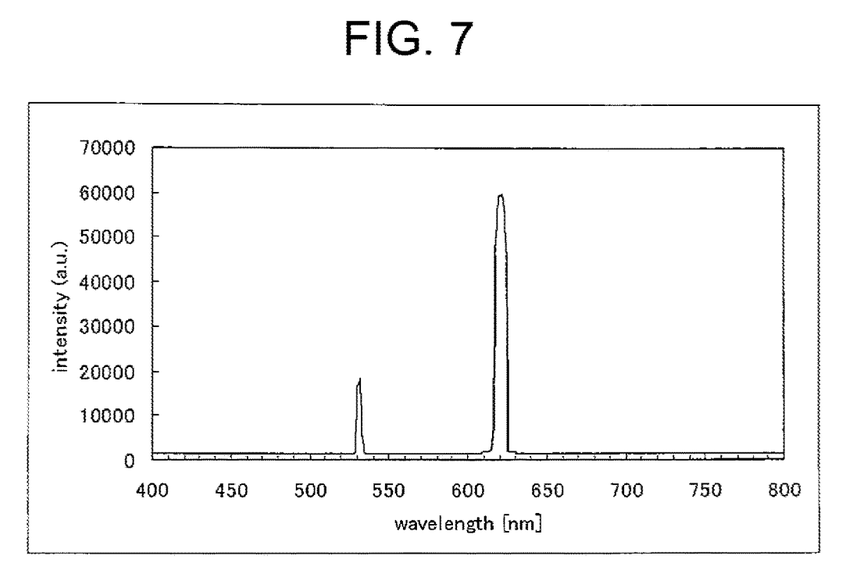
FIG. 7 is a diagram showing an example of a spectrum of outgoing light from a light emission unit measured with a spectrometer when driving two light source units simultaneously.

FIG. 7 is a spectrum of outgoing light from the light emission unit 300 measured with a spectrometer when driving two light source units 100 simultaneously. From the spectrum, it can be seen that lights with wavelengths of 620 nm and 532 nm are being emitted.

Figure 8:
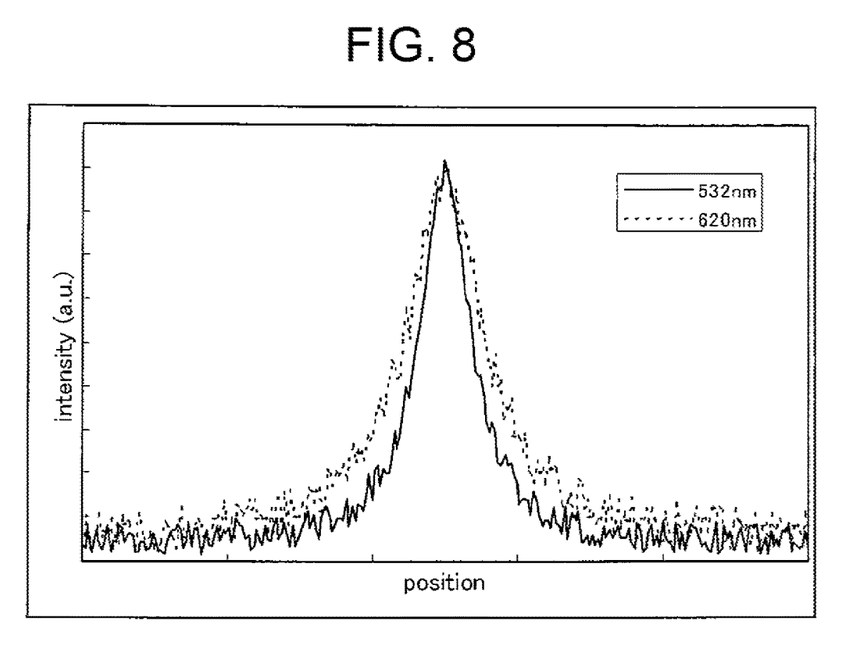
FIG. 8 is a diagram showing the result of measuring each of the profiles of two lights included in outgoing light from the light emission unit.

FIG. 8 shows the result of measuring each of the profiles of the two lights included in the outgoing light from the light emission unit 300. It can be seen that the peak positions of the two lights coincide well spatially.

Also, control of wavelength and light intensity is implemented by controlling the drive current of the light emitting element 110. Firstly, the control unit 420 carries out a switching of outgoing light wavelength (that is, which light source unit 100 is to be caused to operate) in accordance with a switching signal input from the exterior. As a result of this, it is confirmed that a switching of outgoing light wavelength can be carried out at high speed. Also, by changing the size of the drive current of the light emitting element 110, it is possible to change the intensity of the fundamental wave of each light emitting element 110, because of which it is confirmed that it is possible to control the intensity of the outgoing light at high speed.

Also, by modulating the drive current of the fundamental wave of the light emitting element 110, the intensity of the outgoing light of the light emission unit 300 is modulated, and measurement is implemented. It is confirmed that it is possible to measure a faint signal by a lock-in detection of a light receiving side detector signal, with the fundamental wave drive current as a reference signal. Furthermore, it is also confirmed that, even when the two wavelengths λ1 and λ2 are output simultaneously, it is possible, by changing the modulated frequency of each wavelength, to detect the frequencies separately on the light receiving side, that is, it is possible to measure the signal intensities of λ1 and λ2 independently. With this configuration, light source modulation can be carried out at 1.8 GHz.

WORKING EXAMPLE 2

Figure 9A:
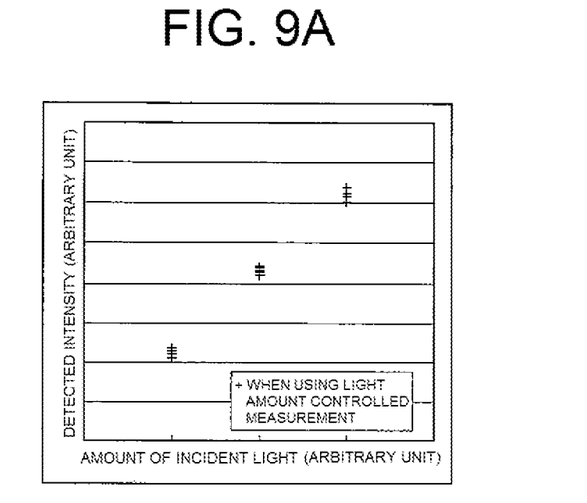
FIGS. 9A and 9B are diagrams showing an advantage of the control shown in FIG. 6.
Figure 9B:
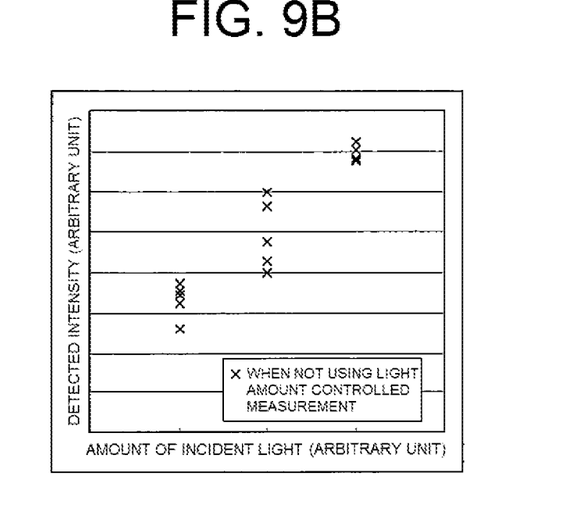

Using the light source device according to the second embodiment, multiple measurements are carried out while increasing the intensity of the outgoing light from the light emission unit 300. Measurement results are shown in FIG. 9. FIG. 9A shows results when using the method described using FIG. 6, while FIG. 9B shows results when not using this method. It can be seen from FIGS. 9A and 9B that measurement reproducibility is better when using the method described using FIG. 6.

Heretofore, a description has been given, referring to the drawings, of embodiments of the invention, but these are exemplifications of the invention, and various configurations other than those heretofore described can also be employed.

[FIG. 1]
410 Driver
420 Control unit
[FIG. 4]
410 Driver
420 Control unit
430 Detection unit
[FIG. 5]
A Degree of light absorption
B Wavelength (nm)
C Degree of oxygen saturation 0%
D Degree of oxygen saturation 100%
[FIG. 6]
A Amount of incident light
B Time
C Amount of diffused and reflected light
D Time
E Light amount threshold value
[FIG. 9(a)]
A Detected intensity (arbitrary unit)
B Amount of incident light (arbitrary unit)
C + When using light amount controlled measurement
[FIG. 9(b)]
A Detected intensity (arbitrary unit)
B Amount of incident light (arbitrary unit)
C × When not using light amount controlled measurement

The invention claimed is:

1. A light source device, comprising:
   one light emission unit from which light is emitted;
   a plurality of light source units that output outgoing light with mutually differing wavelengths;
   a photo coupler that connects the light emission unit and plurality of light source units; and
   a controller that controls the plurality of light source units,
   wherein each of the plurality of light source units includes:
   a light emitting element;
   a wavelength conversion unit, including a phase matching element, that converts a wavelength of light output from the light emitting element, thus generating the outgoing light; and
   a detection unit that detects an intensity of reflected light generated by light emitted from the light emission unit being reflected by a measurement target, wherein
   the controller gradually increases the output of each light emitting element, and stops the increase of the output of each light emitting element when the intensity of the reflected light detected by the detection unit reaches a threshold value or above;
   wherein the threshold value is based on a degree of oxygen saturation in blood; and
   wherein the controller is configured to modulate respective drive currents to modulate respective intensities of simultaneously outgoing light of at least two light emitting elements, and to measure a signal corresponding to the outgoing light intensities at a light receiving side of the detection unit using a fundamental wave drive current as a reference signal.

2. The light source device according to claim 1, wherein the controller causes at least two of the light source units to operate simultaneously, thus causing at least two kinds of the outgoing light to be emitted simultaneously from the light emission unit.

3. The light source device according to claim 1, wherein light emitted from the light emission unit is used as a light source for measuring a saturated oxygen concentration of blood.

4. The light source device according to claim 3, wherein the wavelengths of the outgoing lights output by the plurality of light source units are 490 nm or more, 630 nm or less.

5. The light source device according to claim 2, wherein light emitted from the light emission unit is used as a light source for measuring a saturated oxygen concentration of blood.

6. The light source device according to claim 1, wherein the wavelengths of the outgoing lights output by the plurality of light source units are 490 nm or more, 630 nm or less.

7. The light source device of claim 1, wherein the controller is further configured to change modulated respective frequencies of the outgoing light, and based on detecting the modulated respective frequencies separately at the light receiving side by the detection unit, independently measure an intensity of light of each of the differing wavelengths.

* * * * *